(12) United States Patent
Uckun et al.

(10) Patent No.: US 6,737,537 B2
(45) Date of Patent: May 18, 2004

(54) PLATINUM (II) ANTITUMOR COMPOUNDS (75) Inventors: Faith M. Uckun, White Bear Lake, MN (US); Rama K. Narla, St. Paul, MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 10/146,971

(22) Filed: May 15, 2002

(65) Prior Publication Data

US 2003/0176410 A1 Sep. 18, 2003

Related U.S. Application Data

(63) Continuation of application No. PCT/US00/31297, filed on Nov. 15, 2000.
(60) Provisional application No. 60/165,652, filed on Nov. 15, 1999.

(51) Int. Cl.[7] .......................... C07F 15/00; A61K 31/28
(52) U.S. Cl. ........................ 556/137; 514/492
(58) Field of Search ......................... 556/137; 514/492

(56) References Cited

U.S. PATENT DOCUMENTS

| | | | |
|---|---|---|---|
| 3,892,790 A | 7/1975 | Tobe et al. | 260/429 R |
| 3,904,663 A | 9/1975 | Tobe et al | 260/429 R |
| 4,115,418 A | 9/1978 | Gale et al. | 260/429 R |
| 4,140,707 A | 2/1979 | Cleare et al. | 260/429 R |
| 4,175,133 A | 11/1979 | Gale et al. | 424/287 |
| 4,228,090 A | 10/1980 | Hydes et al. | 260/429 R |
| 4,500,465 A | 2/1985 | Amundsen et al. | 260/429 R |
| 4,559,157 A | 12/1985 | Smith et al. | 252/90 |
| 4,587,331 A | 5/1986 | Hlavka et al. | 536/55 |
| 4,608,392 A | 8/1986 | Jacquet et al. | 514/844 |
| 4,661,516 A | 4/1987 | Brown et al. | 514/492 |
| 4,670,458 A | 6/1987 | Hlavka et al. | 514/492 |
| 4,758,588 A | 7/1988 | Brown et al. | 514/492 |
| 4,820,508 A | 4/1989 | Wortzman | 424/59 |
| 4,938,949 A | 7/1990 | Borch et al. | 424/10 |
| 4,992,478 A | 2/1991 | Geria | 514/782 |
| 5,011,959 A | 4/1991 | Khokhar et al. | 556/137 |
| 5,132,323 A | 7/1992 | Khokhar et al. | 514/492 |
| 5,399,346 A | 3/1995 | Anderson et al. | 424/93.21 |

FOREIGN PATENT DOCUMENTS

| | | |
|---|---|---|
| DE | 4041353 | 12/1990 |
| EP | 0 130 482 | 6/1984 |
| EP | 0 320 960 | 12/1988 |

OTHER PUBLICATIONS

Cleare et al, Bioorganic Chem., 2, 187–210 (1973) Studies on the Antitumor Activity of Group VIII Transition Metal Complexes. Part I. Platinum (II).

Friedman et al., Chimica acta, 91 (1984) 75–80 Studies on the Inhibition of Fumarase and Malate Dehydrogenase by Second Generation Platinum Antitumor Drugs.

Zimmerman et al, Inorganica Chimica Acta, 292 (1999) 127–130 Synthesis and structures of (SP–4–2)–diiodobis(2–hydroxyethylamine)platinum(II), (SP–4–2)–dichlorobis (2–hydroxyethylamine)platinum(II) and (OC–622)–bis(2–hydroxyethylamine)tetrachloroplatinum (IV) in the crystal).

*Primary Examiner*—Porfirio Nazario-Gonzalez
(74) *Attorney, Agent, or Firm*—Merchant & Gould P.C.

(57) ABSTRACT

The present invention describes platinum (II) compounds and compositions useful for treating a subject with a tumor and/or inducing apoptosis in a population of cells. The present invention also describes pharmaceutical compositions containing the aforementioned inventive compound(s) in combination with a pharmaceutically acceptable carrier. Additionally, the invention further provides a method of inducing apoptosis in a population of cells and a method of treating a subject with a tumor, wherein the method comprises administering to the subject a therapeutically effective amount of the aforementioned compound(s) or composition(s).

10 Claims, 2 Drawing Sheets

PLATINUM (II) ANTITUMOR COMPOUNDS

This application is a continuation application of international application Ser. No. PCT/US00/31297 filed on Nov. 15, 2000 claiming priority under 35 U.S.C. 119 (a)–(e) to U.S. Provisional Application No. 60/165,652 filed on Nov. 15, 1999; the international application was published under PCT article 21(2) in English as WO 36431.

FIELD OF THE INVENTION

The present invention relates to platinum (II) compounds effective for treating tumor cells and particularly effective to induce apoptosis in leukemia cells, breast cancer cells, prostate cancer cells, and brain cancer cells.

BACKGROUND OF THE INVENTION

Cancer is a major disease that continues as one of the leading causes of death at any age. In the United States alone, it is anticipated that more than a half a million Americans will die of cancer in 2000. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

The use of platinum (II) compounds as anti-cancer agents has been reported. For example, Cleare et al, Bioorganic Chem., 2, 187–210 (1973) discloses $Pt_2I_2(EA)_2$ and $Pt_2Cl_2(EA)_2$; Friedman et al discloses cis-$Pt(NH_2ETOH)_2Cl_2$; Zimmerman et al, Inorganica Chimica Acta, 292 (1999) 127–130 discloses $Pt_2I_2(EA)_2$ and $Pt_2Cl_2(EA)_2$; U.S. Pat. No. 4,661,516 discloses cyclopropanedicarboxylato(trans-R,R-DACH) Pt(II)H$_2$O; U.S. Pat. No. 4,758,588 discloses cyclopropanedicarboxylato(trans-R,R-DACH) Pt(II)H$_2$O; U.S. Pat. No. 5,011,959 discloses 1,1,-cyclopropanedicarboxylato(trans-R,R-DACH) Pt(II)H$_2$O; and U.S. Pat. No. 5,132,323 discloses 1,1,-cyclopropanedicarboxylato(trans-R,R-DACH) Pt(II)H$_2$O. The present invention describes new platinum (II) compounds which are particularly effective for treating cancer cells.

SUMMARY OF THE INVENTION

In accordance with the purpose(s) of this invention, as embodied and broadly described herein, this invention, in one aspect, relates to platinum (II) compounds including one or more analogues of formula (I):

(I)

wherein:
$R_1$ and $R_2$ are independently halo,
$R_3$, $R_4$, $R_5$ and $R_6$ are independently selected from the group consisting of: hydrogen, hydroxy, ($C_1$–$C_6$) alkyl, ($C_3$–$C_6$) cycloalkyl, ($C_2$–$C_6$) alkenyl, ($C_3$–$C_6$) cycloalkenyl, aryl which may be unsubstituted or substituted with a halo, hydroxy, or ($C_1$–$C_6$) alkyl, ($C_1$–$C_6$) alkoxy, and ($C_1$–$C_6$) hydroxyalkyl, and a) when $R_1=R_2$
$R_7$ and $R_8$ are independently selected from the group consisting of: hydroxy, ($C_3$–$C_6$) alkyl, ($C_3$–$C_6$) cycloalkyl, ($C_2$–$C_6$) alkenyl, ($C_3$–$C_6$) cycloalkenyl, aryl which may be unsubstituted or substituted with a halo, hydroxy, or ($C_1$–$C_6$) alkyl, ($C_1$–$C_6$) alkoxy, and ($C_3$–$C_6$) hydroxyalkyl, or when taken together form a group of the formula:

wherein m is 1 to 5 and $R_{10}$ and $R_{11}$ are independently selected from the group consisting of: hydrogen, halo, hydroxy, ($C_1$–$C_6$) alkyl, ($C_2$–$C_6$) alkenyl, ($C_1$–$C_6$) alkoxy, and ($C_1$–$C_6$) hydroxyalkyl; or b) when $R_1 \neq R_2$,
$R_7$ and $R_8$ are independently selected from the group consisting of: hydroxy, ($C_1$–$C_6$) alkyl, ($C_3$–$C_6$) cycloalkyl, ($C_2$–$C_6$) alkenyl, ($C_3$–$C_6$) cycloalkenyl, aryl which may be unsubstituted or substituted with a halo, hydroxy, or ($C_1$–$C_6$) alkyl, ($C_1$–$C_6$) alkoxy, and ($C_1$–$C_6$) hydroxyalkyl, or when taken together form a group of the formula:

wherein m is 1 to 6 and $R_{10}$ and $R_{11}$ are independently selected from the group consisting of: hydrogen, halo, hydroxy, ($C_1$–$C_6$) alkyl, ($C_2$–$C_6$) alkenyl, ($C_1$–$C_6$) alkoxy, and ($C_1$–$C_6$) hydroxyalkyl;

or a pharmaceutically acceptable salt or ester thereof.

In a second aspect, the invention relates to platinum (II) compounds of formula (I) above, wherein:
$R_1$ and $R_2$ when taken together form a group of the formula:

wherein: n is 1 to 6, and
a) when n=1 to 2,
$R_{12}$ and $R_{13}$ are independently selected from the group consisting of: hydrogen, halo, hydroxy, ($C_1$–$C_6$) alkyl, ($C_2$–$C_6$) alkenyl, ($C_1$–$C_6$) alkoxy, and ($C_1$–$C_6$) hydroxyalkyl, and
$R_7$ and $R_8$ are independently selected from the group consisting of: hydroxy, ($C_1$–$C_6$) alkyl, ($C_3$–$C_6$)

cycloalkyl, $(C_2-C_6)$ alkenyl, $(C_3-C_6)$ cycloalkenyl, aryl which may be unsubstituted or substituted with a halo, hydroxy, or $(C_1-C_6)$ alkyl, $(C_1-C_6)$ alkoxy, and $(C_1-C_6)$ hydroxyalkyl, or when taken together form a group of the formula:

wherein m is 1 to 5 and $R_{10}$ and $R_{11}$ are independently selected from the group consisting of: hydrogen, halo, hydroxy, $(C_1-C_6)$ alkyl, $(C_2-C_6)$ alkenyl, $(C_1-C_6)$ alkoxy, and $(C_1-C_6)$ hydroxyalkyl, or m is 6 and $R_{10}$ and $R_{11}$ are independently selected from the group consisting of: hydrogen, halo, hydroxy, $(C_1-C_6)$ alkyl, $(C_2-C_6)$ alkenyl, $(C_1-C_6)$ alkoxy, and $(C_1-C_6)$ hydroxyalkyl; or b) when n=3 to 6, $R_{12}$ and $R_{13}$ are independently selected from the group consisting of: hydrogen, halo, hydroxy, $(C_1-C_6)$ alkyl, $(C_2-C_6)$ alkenyl, $(C_1-C_6)$ alkoxy, and $(C_1-C_6)$ hydroxyalkyl, and $R_7$ and $R_8$ are independently selected from the group consisting of: hydroxy, $(C_1-C_6)$ alkyl, $(C_3-C_6)$ cycloalkyl, $(C_2-C_6)$ alkenyl, $(C_3-C_6)$ cycloalkenyl, aryl which may be unsubstituted or substituted with a halo, hydroxy, or $(C_1-C_6)$ alkyl, $(C_1-C_6)$ alkoxy, and $(C_1-C_6)$ hydroxyalkyl, or when taken together form a group of the formula:

wherein m is 1 to 6 and $R_{10}$ and $R_{11}$ are independently selected from the group consisting of: hydrogen, halo, hydroxy, $(C_1-C_6)$ alkyl, $(C_2-C_6)$ alkenyl, $(C_1-C_6)$ alkoxy, and $(C_1-C_6)$ hydroxyalkyl;

or a pharmaceutically acceptable salt or ester thereof.

Moreover, the present invention also relates to pharmaceutical compositions containing the aforementioned inventive compound(s) in combination with a pharmaceutically acceptable carrier.

The invention further provides a method of inducing apoptosis in a population of cells, including contacting the population of cells with the aforementioned inventive compound and/or composition(s) comprised of formula (I), wherein:

$R_1$ and $R_2$ are halo or when taken together form a group of the formula:

wherein n is 1 to 6, and $R_{12}$ and $R_{13}$ are independently selected from the group consisting of: hydrogen, halo, hydroxy, $(C_1-C_6)$ alkyl, $(C_2-C_6)$ alkenyl, $(C_1-C_6)$ alkoxy, and $(C_1-C_6)$ hydroxyalkyl;

$R_3$, $R_4$, $R_5$ and $R_6$ are independently selected from the group consisting of: hydrogen, hydroxy, $(C_1-C_6)$ alkyl, $(C_3-C_6)$ cycloalkyl, $(C_2-C_6)$ alkenyl, $(C_3-C_6)$ cycloalkenyl, aryl which may be unsubstituted or substituted with a halo, hydroxy, or $(C_1-C_6)$ alkyl, $(C_1-C_6)$ alkoxy and $(C_1-C_6)$ hydroxyalkyl; and $R_7$ and $R_8$ are independently selected from the group consisting of: hydrogen, hydroxy, $(C_1-C_6)$ alkyl $(C_3-C_6)$ cycloalkyl, $(C_2-C_6)$ alkenyl, $(C_3-C_6)$ cycloalkenyl, aryl which may be unsubstituted or substituted with a halo, hydroxy, or $(C_1-C_6)$ alkyl, $(C_1-C_6)$ alkoxy, and $(C_1-C_6)$ hydroxyalkyl, or when taken together form a group of the formula:

wherein m is 1 to 6, and $R_{10}$ and $R_{11}$ are independently selected from the group consisting of: hydrogen, halo, hydroxy, $(C_1-C_6)$ alkyl, $(C_2-C_6)$ alkenyl, $(C_1-C_6)$ alkoxy, and $(C_1-C_6)$ hydroxyalkyl;

or a pharmaceutically acceptable salt or ester thereof.

In yet another aspect, the invention provides a method of treating a subject with a tumor, wherein the method comprises administering to the subject a therapeutically effective amount of the aforementioned compound(s) or composition (s).

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several experimental examples and together with the description, serve to explain the principles of the invention.

BRIEF DESCRIPTION OF THE DRAWINGS

FIG. 1 shows experimental results for Example 3, including the cell survival rates for differing drug concentrations of the inventive compounds for NALM-6 cells (FIG. 1a) and MOLT-3 cells (FIG. 1b).

FIG. 2 shows experimental results for Example 4, including the cell survival rates for differing drug concentrations of the inventive compounds incubated for 24 hours (FIG. 2a), 48 hours (FIG. 2b), 72 hours (FIG. 2c), and 96 hours (FIG. 2d).

DESCRIPTION OF THE PREFERRED EMBODIMENTS

The present invention may be understood more readily by reference to the following detailed description of preferred embodiments of the invention and the Examples included therein and to the Figures and their previous and following description.

Before the present compounds, compositions, and/or methods are disclosed and described, it is to be understood that this invention is not limited to specific synthetic methods of using or making which may vary. It is also to be understood that the terminology used herein is for the purpose of describing particular embodiments only and is not intended to be limiting.

In this specification and in the claims that follow, reference will be made to a number of terms which shall be defined to have the following meanings:

Reference in the specification and concluding claims to parts by weight of a particular component in a composition, denotes the weight relationship between the component and any other components in the composition for which a part by weight is expressed.

The term "halogen" or "halo" refers to bromine, chlorine, fluorine, and iodine.

The term "alkyl" as used herein refers to a branched or unbranched saturated hydrocarbon group, such as methyl, ethyl, n-propyl, isopropyl, n-butyl, isobutyl, t-butyl, octyl, decyl, tetradecyl, hexadecyl, eicosyl, tetracosyl and the like. The alkyl group may have one or more hydrogen atoms replaced with a functional group. The term "cycloalkane" as used herein refers to a cyclic alkane group.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms.

The term "alkenyl" as used herein refers to a branched or unbranched mon-unsaturated or di-unsaturated hydrocarbon group, which may have one or more hydrogen atoms replaced with a functional group. Geometric structures such as (AB)C=C(CD) are intended to include all isomers. The term "cycloalkenyl" as used herein refers to a cyclic alkenyl group.

The term "aryl" as used herein refers to a $C_6H_6$ aromatic ring. Substituents on the aryl group may be present on any position, i.e. ortho, meta or para positions or fused to the aromatic ring.

By "hydroxyalkyl" is meant a branched, unbranched, or cyclic saturated hydrocarbon group with a terminal hydroxy group, such as methanol, ethanol,n-propanol, isopropanol, n-butanol, isobutanol, t-butanol, octanol, decanol, tetradecanol, hexadecanol and the like. The alkyl group may have one or more hydrogen atoms replaced with a functional group.

By "platinum (II) compound" or "platinum (II) analogue" it is meant to include compounds of the formula (I):

wherein:

$R_1$ and $R_2$ are halo or when together form a group of the formula:

wherein n is 1 to 6, and $R_{12}$ and $R_{13}$ are independently selected from the group consisting of: hydrogen, halo, hydroxy, ($C_1$–$C_6$) alkyl ($C_2$–$C_6$) alkenyl, ($C_1$–$C_6$) alkoxy, and ($C_1$–$C_6$) hydroxyalkyl;

$R_3$, $R_4$, $R_5$ and $R_6$ are independently selected from the group consisting of: hydrogen, hydroxy, ($C_1$–$C_6$) alkyl, ($C_3$–$C_6$) cycloalkyl, ($C_2$–$C_6$) alkenyl, ($C_3$–$C_6$) cycloalkenyl, aryl which may be unsubstituted or substituted with a halo, hydroxy, or ($C_1$–$C_6$) alkyl, ($C_1$–$C_6$) alkoxy, and ($C_1$–$C_6$) hydroxyalkyl; and $R_7$ and $R_8$ are independently selected from the group consisting of: hydrogen, hydroxy, ($C_1$–$C_6$) alkyl, ($C_3$–$C_6$) cycloalkyl, ($C_2$–$C_6$) alkenyl, ($C_3$–$C_6$) cycloalkenyl, aryl which may be unsubstituted or substituted with a halo, hydroxy, or ($C_1$–$C_6$) alkyl, ($C_1$–$C_6$) alkoxy, and ($C_1$–$C_6$) hydroxyalkyl, or when taken together form a group of the formula:

wherein m is 1 to 6, and $R_{10}$ and $R_{11}$ are independently selected from the group consisting of: hydrogen, halo, hydroxy, ($C_1$–$C_6$) alkyl ($C_2$–$C_6$) alkenyl, ($C_1$–$C_6$) alkoxy, and ($C_1$–$C_6$) hydroxyalkyl;

or a pharmaceutically acceptable salt or ester thereof.

By "apoptosis" is meant cell death, inhibition of clonogenic growth, and cytotoxicity. Therefore, inducing apoptosis includes inducing cell death, inhibiting clonogenic growth, and inducing cytotoxicity.

As used throughout, by "contacting" is meant an instance of exposure of at least one cell (e.g., a neural cell, a stem cell, a cardiac cell) to an agent (e.g., a platinum (II) compound).

As used herein, the term "cancer" or "tumor" includes cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; myeloma; melanoma of cutaneous and intraocular origin; childhood leukemia and lymphomas, Hodgkin's disease, lymphomas of lymphocytic and cutaneous origin, acute and chronic leukemia, plasma cell neoplasm and cancers associated with AIDS. In one embodiment, cancer is not Sarcoma 180. The preferred mammalian species for treatment are humans and domesticated animals.

The term "subject" is meant an individual. Preferably, the subject is a mammal such as a primate, and more preferably, a human. Thus, the "subject" can include domesticated animals (e.g., cats, dogs, etc.), livestock (e.g., cattle, horses, pigs, sheep, goats, etc.), and laboratory animals (e.g., mouse, rabbit, rat, guinea pig, etc.).

In general, "therapeutically effective amount" or "therapeutically effective dose" means the amount needed to achieve the desired result or results (reducing or delaying apoptosis or treating a degenerative condition). One of ordinary skill in the art will recognize that the potency and, therefore, a "therapeutically effective amount" can vary for the various platinum (II) compounds used in the invention. One skilled in the art can readily assess the potency of the compounds.

By "pharmaceutically acceptable" is meant a material that is not biologically or otherwise undesirable, i.e., the material may be administered to an individual along with the selected bicyclic compound without causing any undesirable biological effects or interacting in a deleterious manner with any of the other components of the pharmaceutical composition in which it is contained.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to 100° C., preferably at room temperature. The molar ratio of compounds of structural formula (I) to base used are chosen to provide the ratio desired for any particular salts. For preparing, for example, the ammonium salts of the free acid starting material, a particular preferred embodiment, the starting material can be treated with approximately one equivalent of base to yield a salt. When calcium salts are prepared, approximately one-half a molar equivalent of base is used to yield a neutral salt, while for aluminum slats, approximately one-third a molar equivalent of base will be used.

Ester derivatives are typically prepared as precursors to the acid form of the compounds, and accordingly may serve as prodrugs. Generally, these derivatives will be alkyl esters such as methyl, ethyl, and the like. Amide derivatives/—(CO)NH$_2$, —(CO)NHR and —(CO)NR$_2$, where R is alkyl, may be prepared by reaction of the carboxylic acid-containing compound with ammonia or a substituted amine.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents.

Preferred constituents of $R_1$ and $R_2$ for the compounds of formula I are: where $R_1=R_2$, Cl, Br, or I, or where $R_1$ and $R_2$ when taken together form a group of the formula:

n is preferably 1 to 3, more preferably 3; and $R_{12}$ and $R_{13}$ are hydrogen, halo, or hydroxy, more preferably hydrogen.

Preferred constituents of $R_3$, $R_4$, $R_5$, and $R_6$ are hydrogen, hydroxy, and $C_1$–$C_6$ alkyl, more preferably hydrogen or $C_1$–$C_3$ alkyl.

Preferred constituents of $R_7$ and $R_8$ are hydrogen, $C_1$–$C_6$ alkyl, or $R_7$ and $R_8$ when taken together form a group of the formula:

wherein m is preferably 1 to 6 and $R_{10}$ and $R_{11}$ are preferably hydrogen, $C_1$–$C_6$ alkyl or halo, most preferably hydrogen.

Particularly useful compounds of formula (I) include:

Synthetic Methods

The compounds of the present invention may be readily synthesized using techniques generally known to synthetic organic chemists. Suitable experimental methods for making and derivatizing aromatic compounds are described, for example, in the references cited in the Background section herein, the disclosures of which are hereby incorporated by reference for their general teachings and for their synthesis teachings. Although any known synthetic route may be used, preferred routes are illustrated by way of example in scheme 1.

Scheme 1

Utility and Administration

The compounds of formula (I) as above defined may be useful in inducing apoptosis in a population of cells, and/or treating a subject with a tumor.

The methods include contacting the cells with a compound or composition of formula (I) as defined above, or administering to the subject a therapeutically effective amount of a compound or composition of formula (I). In one embodiment, the cells are lymphoblastic leukemia cells, multiple myeloma cells, breast cancer cells, prostate cancer cells, brain tumor cells, neural tumor cells, or neuronal tumor cells. The tumor cells include malignant and benign tumor cells.

It is well known in the art how to determine antitumor activity or cytotoxicity using the standard tests described herein, or using other similar tests. Preferably, the apoptosis would result in at least a 10% reduction in the number of cells, including, for example, 15%, 20%, 25%, 30%, 40%, 50%, 60%, 70%, 80%, 90%, 100%, or any amount in between.

The reduction can be measured, for example, by comparing the number of cells after contact with the platinum (II) compound to the number of cells in a jig control population of cells lacking contact with the platinum (II) compound. Histological signs of apoptosis in cells after contact with the platinum (II) compound include condensation of the chromatin, the occurrence of apoptotic bodies, and cellular shrinkage. DNA laddering and other signs of DNA degradation are also signs of apoptosis. Apoptosis can also be assessed indirectly by observing, for example, a reduction in the amount of release or activity by the population of cells. Thus, if the cell population undergoes apoptosis, a decrease in neurotransmitter release upon stimulation or neuronal cells would decrease.

The cells can be contacted in vitro with the platinum (II) compound, for example, by adding the compound to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of "contact" with a cell or population of cells is determined by the time the compound is present at physiologically effective levels or at presumed physiologically effective levels in the medium or extracellular fluid bathing the cell or cells. Preferably, the duration of contact is 1–96 hours, and more preferably, for 24 hours, but such time would vary based on the half life of the compound and could be optimized by one skilled in the art using routine experimentation.

The platinum (II) compounds can be formulated as pharmaceutical compositions and administered to a mammalian host, such as a human patient or a domestic animal in a variety of forms adapted to the chosen route of administration, i.e., orally or parenterally, by intravenous, intramuscular, topical or subcutaneous routes.

The platinum (II) compounds of the present invention can also be administered using gene therapy methods of delivery. See, e.g., U.S. Pat. No. 5,399,346, which is incorporated by reference in its entirety. Using a gene therapy method of delivery, primary cells transfected with the gene for the compound of the present invention can additionally be transfected with tissue specific promoters to target specific organs, tissue, grafts, tumors, or cells.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of odurse, be varied and may conveniently be between about 2 to about 60% of the weight of a given unit dosage form. The amount of active compound in such therapeutically useful compositions is such that an effective dosage level will be obtained.

The tablets, dragees, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. Also the dosage of the compound varies depending on the target cell, tumor, tissue, graft, or organ.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound may conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infuisions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

Experimental

The following examples are put forth so as to provide those of ordinary skill in the art with a complete disclosure and description of how the compounds, compositions, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

EXAMPLE 1

The following illustrate representative pharmaceutical dosage forms, containing a compound of formula I ('Compound of formula I'), for therapeutic or prophylactic use in humans.

| (i) Tablet 1 | mg/tablet |
|---|---|
| Compound of formula I | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound of formula I | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound of formula I | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound of formula I (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| Compound of formula I (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| Compound of formula I | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

EXAMPLE 2

The following compounds of formula I were synthesized via scheme 1.

(1) DDE246: cis-[PtI$_2$(NH$_2$C$_2$H$_4$OH)$_2$] with the chemical formula (1):

(1)

(2) DDE247: cis-[PtCl$_2$(NH$_2$C$_2$H$_4$OH)$_2$] with the chemical formula (2):

(2)

(3) DDE248: cis-[Pt(CPDCA)(NH$_2$C$_2$H$_4$OH)$_2$] with the chemical formula (3):

(3)

(4) DDE249: cis-[PtI$_2$(NH$_2$C$_3$H$_6$OH)$_2$] with the chemical formula (4):

(4)

(5) DDE250: cis-[Pt(CPDCA)(DACH)]H$_2$O with the chemical formula (5):

(5)

(6) DDE173: cis-[Pt(CPDCA)(NH$_3$)$_2$]H$_2$O with the chemical formula (6):

(6)

Wherein
CPDCA=cyclopropane-1,1-dicarboxylic acid
DACH=trans-1,2-diaminocyclohexane Elemental analysis was performed on the compounds resulting in the values shown in table 1.

TABLE 1

| Compound | C found (calc) | H found (calc) | N found (calc) |
|---|---|---|---|
| (1) DDE246 | 8.53 (8.41) | 2.45 (2.47) | 4.91 (4.91) |
| (2) DDE247 | 12.37 (12.38) | 3.62 (3.64) | 7.05 (7.22) |
| (3) DDE248 | 24.46 (24.27) | 4.12 (4.07) | 6.03 (6.29) |
| (4) DDE249 | 12.11 (12.03) | 3.07 (3.03) | 4.67 (4.68) |
| (5) DDE250 | 29.34 (29.01) | 4.42 (4.43) | 6.21 (6.15) |
| (6) DDE173 | 16.02 (16.00) | 3.21 (3.22) | 7.57 (7.47) |

HNMR analysis were performed on the synthesized compounds resulting in the values shown in table 2.

TABLE 2

| Compound | Solvent | Chemical Shift (ppm) |
|---|---|---|
| (1) DDE246 | D$_2$O | 2.97~3.09(m, 4H, a), 3.86~3.88(t, 4H, b) |
| (2) DDE247 | D$_2$O | 2.82~2.93(m, 4H, a), 3.85~3.88(t, 4H, b) |
| (3) DDE248 | D$_2$O | 1.57(s, 4H, c & d), 2.72~2.79(m, 4H, a), 3.85~3.89(t, 4H, b) |
| (4) DDE249 | D$_2$O | 1.90~1.99(m, 4H, b), 2.92~3.04(m, 4H, a), 3.69~3.74(t, 4H, c) |
| (5) DDE250 | DMSO-d$_6$ | 0.96~1.02(t, 2H, e' & f), 1.11~1.22(m, 6H, i & j & d' & g'), 1.44~1.46(d, 2H, e & f), 1.78~1.82(d, 2H, d & g), 2.06(br, 2H, c & h), 5.22~5.28(t, 2H, N$_a$H' & N$_b$H'), 5.88~5.90(d, 2H, N$_a$H & N$_b$H) |
| (6) DDE173 | D$_2$O | 1.571 & 1.577(d, 4H, a & b) |

EXAMPLE 3

Figure 1A:
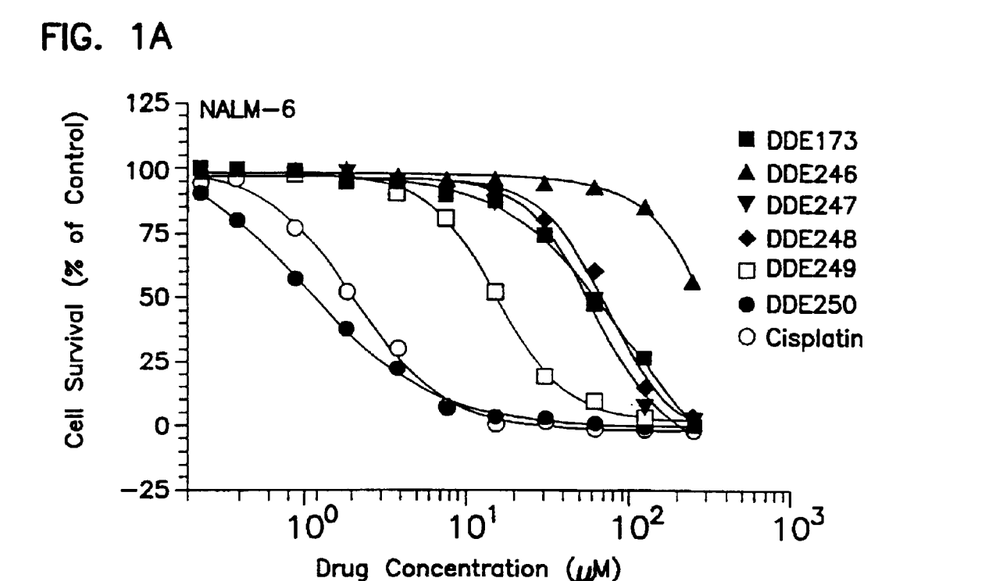
Figure 1B:
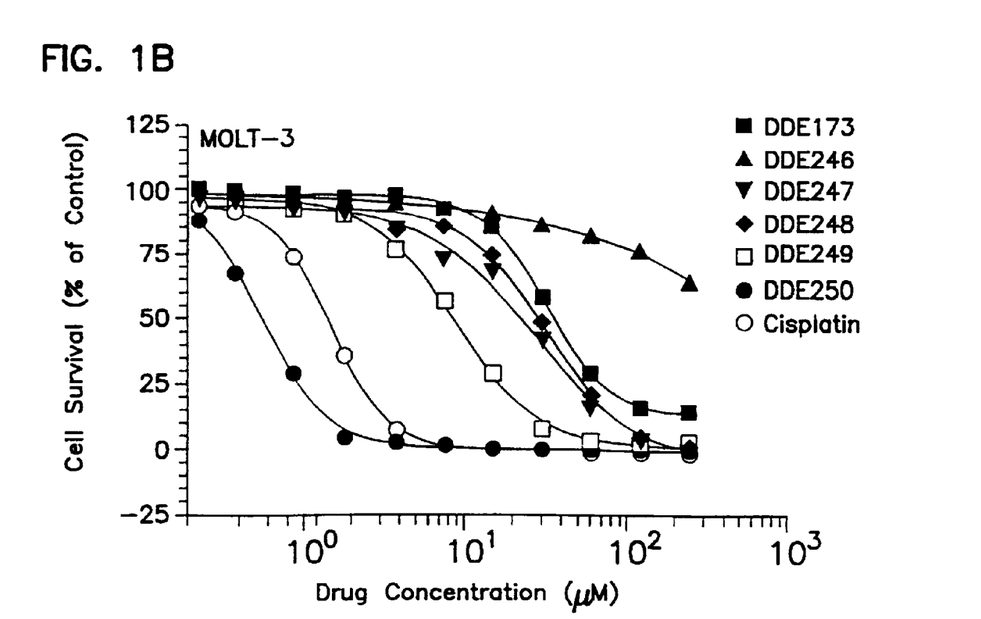

In vitro cytotoxic activity of compounds (1)–(6) as synthesized and described in example 2 and of cisplatin was measured for human B-lineage acute lymphoblastic leukemia (NALM-6) and T-lineage acute lymphoblastic leukemia (MOLT-3) cells. The cells were incubated with concentrations ranging from 0.1 μM to 250 μM of the appropriate compound in 96-well plates for 48 hours. Cytotoxicity was determined by MTT [(3-[4,5-dimethylthiazol-2-yl]-2,5-diphenyl tetrazolium bromide)] assays. The results are graphed in FIG. 1a for NALM-6 cells and FIG. 1b for MOLT-3 cells.

EXAMPLE 4

Figure 2A:
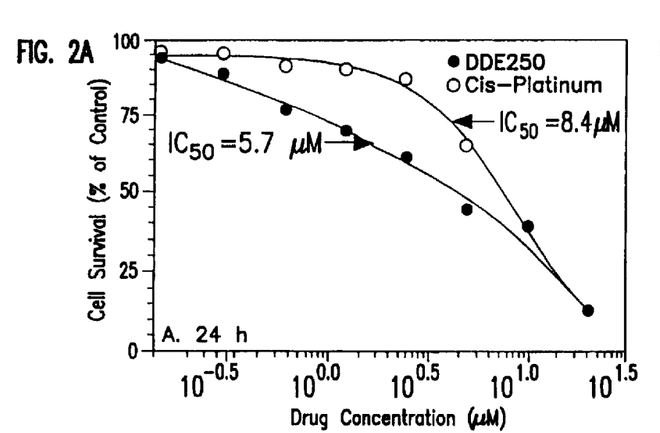
Figure 2B:
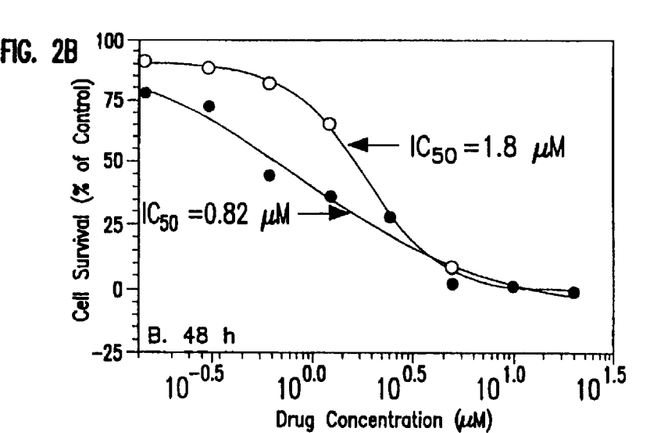
Figure 2C:
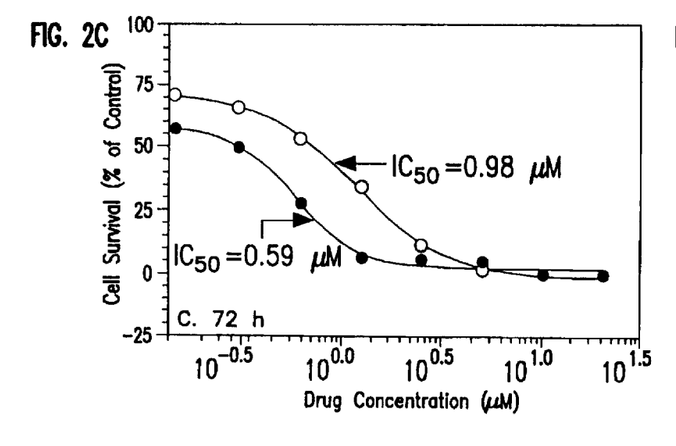
Figure 2D:
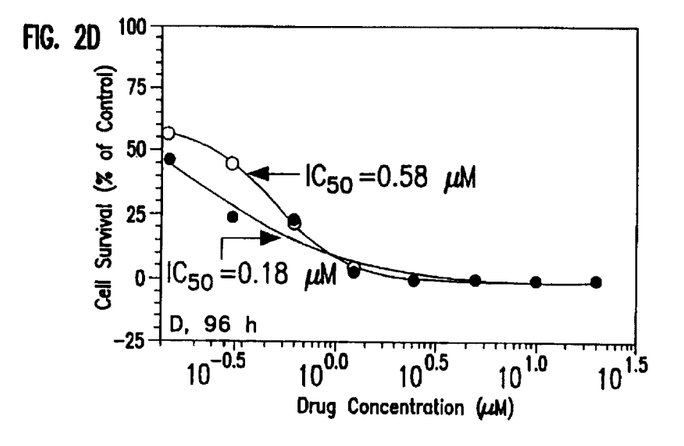

In vitro cytotoxic activity of compound (5) as synthesized and described in example 2 and of cisplatin was measured for human B-lineage acute lymphoblastic leukemia (NALM-6) cells. The cells were incubated with concentrations ranging from 0.2 μM to 20 μM of the appropriate compound in 96-well plates for 24 hours, 48 hours, 72 hours, and 96 hours. Cytotoxicity was determined by MTT assays and the IC$_{50}$ values were determined using Graphpad Prism Software. The results are graphed in FIG. 2a for incubation of 24 hours, FIG. 2b for incubation of 48 hours, FIG. 2c for incubation of 72 hours, and FIG. 2d for incubation of 96 hours.

EXAMPLE 5

Various cells were incubated with the compounds (1)–(6) as synthesized and described in example 2 and with cisplatin in 96-well plates for 48 hours. Cytotoxicity was determined by MTT assays and the IC$_{50}$ values were determined using Graphpad Prism Software. The results are shown in table 3.

TABLE 3

| | IC$_{50}$ [MTT Assays] ($\mu$M) | | | | | | | |
|---|---|---|---|---|---|---|---|---|
| Compound | NALM-6 (Leukemia) | MOLT-3 (Leukemia) | U266BL (Multiple Myeloma) | HS-Sultan (Multiple Myeloma) | BT-20 (Breast Cancer) | MDA-MB-231 (Breast Cancer) | PC3 (Prostate Cancer) | U373 (Brain Tumor) |
| (1) DDE246 | >250 | >250 | >250 | >250 | >250 | >250 | >250 | >250 |
| (2) DDE247 | 60.1 ± 3.8 | 30.4 ± 4.3 | 35.6 ± 6.1 | 22.4 ± 2.8 | 51.4 ± 6.1 | 80.1 ± 5.5 | 91.3 ± 57.1 | 48.3 ± 2.8 |
| (3) DDE248 | 75.3 ± 5.2 | 33.5 ± 4.5 | N.D. | N.D. | 48.9 ± 7.3 | N.D. | 248.1 ± 9.3 | 129.5 ± 8.2 |
| (4) DDE249 | 16.5 ± 6.5 | 9.5 ± 3.4 | N.D. | N.D. | 81.3 ± 5.9 | N.D. | >250 | >250 |
| (5) DDE250 | 0.45 ± 0.02 | 0.66 ± 0.01 | 18.6 ± 2.1 | 21.5 ± 3.5 | 21.3 ± 3.1 | 38.5 ± 6.4 | >250 | >250 |
| (6) DDE173 | 90.8 ± 6.2 | 41.8 ± 3.5 | N.D. | N.D. | >250 | N.D. | >250 | >250 |
| Cisplatin | 1.1 ± 0.02 | 1.04 ± 0.02 | 15.6 ± 3.5 | 31.8 ± 7.2 | 7.21 ± 3.5 | 51.6 ± 6.8 | >250 | >250 |

EXAMPLE 6

The effectiveness of inducing apoptosis by compound (5) as synthesized and described in example 2 was measured for human B-lineage acute lymphoblastic leukemia (NALM-6) cells, T-lineage acute lymphoblastic leukemia (MOLT-3) cells, and multiple myeloma (ARH-77) cells. The cells were incubated with concentrations of 5 $\mu$M of compound (5) in 96-well plates 48 hours. An in situ apoptosis assay, which allows the detection of exposed 3'-hydroxyl groups in fragmented DNA by TdT-mediated dUTP nick-end labeling (TUNEL), was used by fixing, permeabilizing and visualizing the DNA degradation. Apoptotic nuclei were detected visually with a color change. The amount of apoptotic nuclei of the control cells (not incubated with compound (5)) and the incubated cells were compared. In all cell lines, the compound (5) greatly increased apoptosis over the control.

EXAMPLE 7

The effect on clonogenic growth of human cancer cell lines was determined for compound (5) as synthesized and described in example 2 and cisplastin for human B-lineage acute lymphoblastic leukemia (NALM-6) cells and T-lineage acute lymphoblastic leukemia (MOLT-3) cells. The cells were incubated with concentrations ranging from 0 (control) to 10 $\mu$M of the appropriate compound for 24 hours at 37° C. in a humidified 5% $CO_2$ atmosphere. The cells were then resuspended in clonogenic a-MEM medium containing 0.9% methyl cellulose. $1 \times 10^4$ cells/dish were plated in 35 mm Petri dishes and cultured for 7 days at 37° C. in a humidified 5% $CO_2$ atmosphere. The colonies containing ≧20 cells were counted using an inverted phase microscope. The results are shown below in table 4.

TABLE 4

| Compound | Cell Line | Concentration ($\mu$M) | Mean No. of Colonies/$10^5$ cells | % Inhibition |
|---|---|---|---|---|
| (5) DDE250 | NALM-6 | 0 (control) | 3696 (3056, 4336) | — |
| (5) DDE250 | NALM-6 | 0.01 | 2110 (1928, 2292) | 42.9 |
| (5) DDE250 | NALM-6 | 0.1 | 1908 (1886, 1930) | 48.4 |
| (5) DDE250 | NALM-6 | 1 | 248 (228, 268) | 93.3 |
| (5) DDE250 | NALM-6 | 10 | 0 | >99.9 |
| Cisplatin | NALM-6 | 0 (control) | 3696 (3056, 4336) | — |
| Cisplatin | NALM-6 | 0.01 | 2044 (1996, 2092) | 44.7 |
| Cisplatin | NALM-6 | 0.1 | 1832 (1744, 1920) | 50.4 |
| Cisplatin | NALM-6 | 1 | 514 (470, 558) | 86.0 |
| Cisplatin | NALM-6 | 10 | 0 | >99.9 |
| (5) DDE250 | MOLT-3 | 0 (control) | 3656 (3364, 3948) | — |
| (5) DDE250 | MOLT-3 | 0.01 | 1182 (1080, 1284) | 67.7 |
| (5) DDE250 | MOLT-3 | 0.1 | 1188 (1095, 1281) | 67.5 |
| (5) DDE250 | MOLT-3 | 1 | 179 (170, 188) | 95.1 |
| (5) DDE250 | MOLT-3 | 10 | 0 | >99.9 |
| Cisplatin | MOLT-3 | 0 (control) | 3656 (3364, 3948) | — |
| Cisplatin | MOLT-3 | 0.01 | 1280 (1220, 1340) | 64.9 |
| Cisplatin | MOLT-3 | 0.1 | 1168 (1116, 1220) | 68.0 |
| Cisplatin | MOLT-3 | 1 | 241 (236, 246) | 93.4 |
| Cisplatin | MOLT-3 | 10 | 0 | >99.9 |

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of formula I:

(I)

wherein:
  $R_1$ and $R_2$ are independently chloro, iodo, or bromo,
  $R_3$, $R_4$, $R_5$ and $R_6$ are independently hydrogen, hydroxy, ($C_1$–$C_6$) alkyl, ($C_3$–$C_6$) cycloalkyl, ($C_2$–$C_6$) alkenyl, ($C_3$–$C_6$) cycloalkenyl, ($C_1$–$C_6$) alkoxy, ($C_1$–$C_6$) hydroxyalkyl, or aryl, wherein the aryl can be substituted with a halo, hydroxy, or ($C_1$–$C_6$) alkyl, and
  a) when $R_1$=$R_2$=chloro
    $R_7$ and $R_8$ are independently hydroxy, ($C_2$–$C_6$) alkenyl, ($C_3$–$C_6$) cycloalkenyl, ($C_1$–$C_6$) alkoxy, methanol, n-propanol, isobutanol, t-butanol, octanol, decanol, tetradecanol, hexadecanol, aryl, wherein the aryl can be substituted with a halo, hydroxy, or ($C_1$–$C_6$) alkyl, or when taken together $R_7$ and $R_8$ form a group of the formula:

wherein m is 1 to 5 and $R_{10}$ and $R_{11}$ are independently hydrogen, halo, hydroxy, ($C_1$–$C_6$) alkyl, ($C_2$–$C_6$) alkenyl, ($C_1$–$C_6$) alkoxy, or ($C_1$–$C_6$) hydroxyalkyl, with the proviso that $R_{10}$ and $R_{11}$ are not both hydrogen or hydroxy when m=4; or b) when $R_1$=$R_2$=iodo

$R_7$ and $R_8$ are independently hydroxy, ($C_2$–$C_6$) alkyl, ($C_3$–$C_5$) cycloalkyl, ($C_2$–$C_6$) alkenyl, ($C_3$–$C_6$) cycloalkenyl, ($C_1$–$C_6$) alkoxy, ($C_5$–$C_6$) hydroxyalkyl, aryl, wherein the aryl can be substituted with a halo, hydroxy, or ($C_1$–$C_6$) alkyl, or when taken together $R_7$ and $R_8$ form a group of the formula:

wherein m is 1 to 5 and $R_{10}$ and $R_{11}$ are independently hydrogen, halo, hydroxy, ($C_1$–$C_6$) alkyl, ($C_2$–$C_6$) alkenyl, ($C_2$–$C_6$) alkoxy, or ($C_1$–$C_6$) hydroxyalkyl, with the proviso that $R_{10}$ and $R_{11}$ are not both hydroxy when m=4; or c) when $R_1$=$R_2$=bromo

$R_7$ and $R_8$ are independently hydroxy, ($C_3$–$C_6$) alkyl, ($C_3$–$C_5$) cycloalkyl, ($C_2$–$C_6$) alkenyl, ($C_3$–$C_6$) cycloalkenyl, ($C_1$–$C_6$) alkoxy, ($C_2$–$C_6$) hydroxyalkyl, aryl, wherein the aryl can be substituted with a halo, hydroxy, or ($C_1$–$C_6$) alkyl, or when taken together $R_7$ and $R_8$ form a group of the formula:

wherein m is 1 to 5 and $R_{10}$ and $R_{11}$ are independently hydrogen, halo, hydroxy, ($C_1$–$C_6$) alkyl, ($C_2$–$C_6$) alkenyl, ($C_2$–$C_6$) alkoxy, or ($C_2$–$C_6$) hydroxyalkyl, with the proviso that $R_{10}$ and $R_{11}$ are not both hydroxy when m=4; or d) when $R_1 \neq R_2$, $R_7$ and $R_8$ are independently hydroxy, ($C_1$–$C_6$) alkyl, ($C_3$–$C_6$) cycloalkyl, ($C_2$–$C_6$) alkenyl, ($C_3$–$C_6$) cycloalkenyl, ($C_1$–$C_6$) alkoxy, ($C_1$–$C_6$) hydroxyalkyl, aryl, wherein the aryl can he substituted with a halo, hydroxy, or ($C_1$–$C_6$) alkyl, or when taken together $R_7$ and $R_8$ form a group of the formula:

wherein m is 1 to 5 and $R_{10}$ and $R_{11}$ are independently hydrogen, halo, hydroxy, ($C_1$–$C_6$) alkyl, ($C_2$–$C_6$) alkenyl, ($C_1$–$C_6$) alkoxy, or ($C_1$–$C_6$) hydroxyalkyl, with the proviso that $R_{10}$ and $R_{11}$ are not both hydroxy when m=4;

or a pharmaceutically acceptable salt or ester thereof.

2. The compound of claim 1, wherein the $R_3$, $R_4$, $R_5$, and $R_6$ are independently hydrogen, hydroxy, or ($C_1$–$C_3$) alkyl.

3. The compound of claim 1, wherein $R_3$, $R_4$, $R_5$, and $R_6$ are hydrogen.

4. A compound:

or a pharmaceutically acceptable salt or ester thereof.

5. A pharmaceutical composition comprising a compound of claim 1 and a pharmaceutically acceptable carrier.

6. A pharmaceutical composition comprising a compound of claim 4 and a pharmaceutically acceptable carrier.

7. A method of inducing apoptosis in a population of cells, comprising contacting a population of lymphoblastic leukemia cells, multiple myeloma cells, breast cancer cells, prostate cancer cells, or brain tumor cells with a compound according to claim 1.

8. The method of claim 7, wherein the compound is:

or a pharmaceutically acceptable salt or ester thereof.

9. The method of claim 15, wherein the compound is:

10. A method of inducing apoptosis in a population of cells, comprising contacting a population of lymphoblastic leukemia cells, multiple myeloma cells, breast cancer cells, prostate cancer cells, or brain tumor cells with a compound:

-continued

,

I, or

-continued

.

* * * * *

UNITED STATES PATENT AND TRADEMARK OFFICE
CERTIFICATE OF CORRECTION

PATENT NO. : 6,737,537 B2
DATED : May 18, 2004
INVENTOR(S) : Uckun et al.

It is certified that error appears in the above-identified patent and that said Letters Patent is hereby corrected as shown below:

Title page,
Item [56], References Cited, OTHER PUBLICATIONS, insert -- Chemical Abstracts, abstract no. 68562, Vol. 112, 1990. --

Column 19,
Line 36, "($C_2$-$C_6$) alkoxy," should read -- ($C_1$-$C_6$) alkoxy, --

Column 20,
Line 45, "claim 15," should read -- claim 7, --

Signed and Sealed this

Tenth Day of August, 2004

JON W. DUDAS
*Acting Director of the United States Patent and Trademark Office*